US00PP14463P29

(12) United States Plant Patent
Heims

(10) Patent No.: US PP14,463 P2
(45) Date of Patent: Jan. 13, 2004

(54) *CAREX SIDEROSTICHA* PLANT NAMED 'LEMON ZEST'

(50) Latin Name: *Carex siderosticha*
Varietal Denomination: Lemon Zest

(75) Inventor: Daniel M. Heims, Portland, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 10/453,242

(22) Filed: Jun. 2, 2003

(51) Int. Cl.[7] ..... A01H 5/00
(52) U.S. Cl. ..... Plt./373
(58) Field of Search ..... Plt./373

*Primary Examiner*—Bruce R. Campell
*Assistant Examiner*—W C Haas
(74) *Attorney, Agent, or Firm*—Klarquist Sparkman, LLP

(57) ABSTRACT

A new and distinct cultivar of *Carex siderosticha* plant called 'Lemon Zest' characterized by bright chartreuse foliage.

1 Drawing Sheet

Botanical classification: *Carex siderosticha.*
Variety denomination: 'Lemon Zest'.

BACKGROUND OF THE INVENTION

The present invention relates to a new and distinct cultivar of a hardy, suffrutescent perennial, *Carex siderosticha,* known by the cultivar name of 'Lemon Zest'. The genus Carex is a member of the family Cyperaceae.

The new cultivar originated as a chance mutation in tissue culture of *Carex siderosticha* 'Banana Boat' (an unpatented plant with yellow leaves and green margins).

SUMMARY OF THE INVENTION

This new cultivar is unique and characterized by: Lemon yellow spring leaves turning chartreuse to light green as the summer progresses.

This new cultivar has been reproduced only by asexual propagation (division and tissue culture). Each of the progeny exhibits identical characteristics to the original plant. Asexual propagation by tissue culture using standard micropropagation techniques with lateral shoots as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE PHOTOGRAPH

The photograph shows a two-year-old plant growing in a 1 gallon container in April in Canby, Oreg.

DETAILED PLANT DESCRIPTION

The following is a detailed description of the new cultivar based on observations of two-year-old specimens grown in containers in Canby, Oreg. The color descriptions are all based on The Royal Horticultural Society Colour Chart.

Botanical name: *Carex siderosticha.*
Cultivar name: 'Lemon Zest'.

Plant:
- *Type.*—Rhizomatous, herbaceous perennial.
- *Form.*—Clumping.
- *Hardiness.*—USDA Zone 6 to 9.
- *Size.*—15 cm tall and 33 cm wide.
- *Habit.*—Slow creeping by rhizomes.

Leaf:
- *Type.*—Simple, deciduous.
- *Arrangement.*—Basal, in three ranks.
- *Shape.*—Linear-lanceolate.
- *Venation.*—Parallel.
- *Margins.*—Entire.
- *Apex.*—Acuminate.
- *Base.*—Sheathed.
- *Blade size.*—13 to 30 cm long and 12 to 25 mm wide.
- *Vestiture.*—Glabrous.
- *Aspect.*—Matte.
- *Texture.*—Papery.
- *Leaf color.*—Spring: Topside — Yellow Green. New spring growth is between Yellow Green 151B and 154B. They become greener with age to Yellow Green 145A. The new shoots are tinged pink, Greyed Red 181D. Bottom side — Same. Summer: Topside — Yellow Green 145A to Yellow Green 146C. Bottom side — Same.

Flower, inflorescence, seed, fruit: Insignificant and the same as the species.

Disease tolerance: Excellent like the species.

Comparisons to similar *Carex siderosticha*: There are no other all gold forms of *Carex siderosticha.* Compared to *Carex siderosticha* 'Banana Boat' (an unpatented plant), this new cultivar has all yellow to yellow-green foliage rather than being edged green with a yellow center.

Growing conditions: This new variety prefers rich, moist soil in shade or filtered light.

I claim:

1. A new and distinct cultivar of *Carex siderosticha* plant, substantially as shown and described, characterized by bright chartreuse foliage.

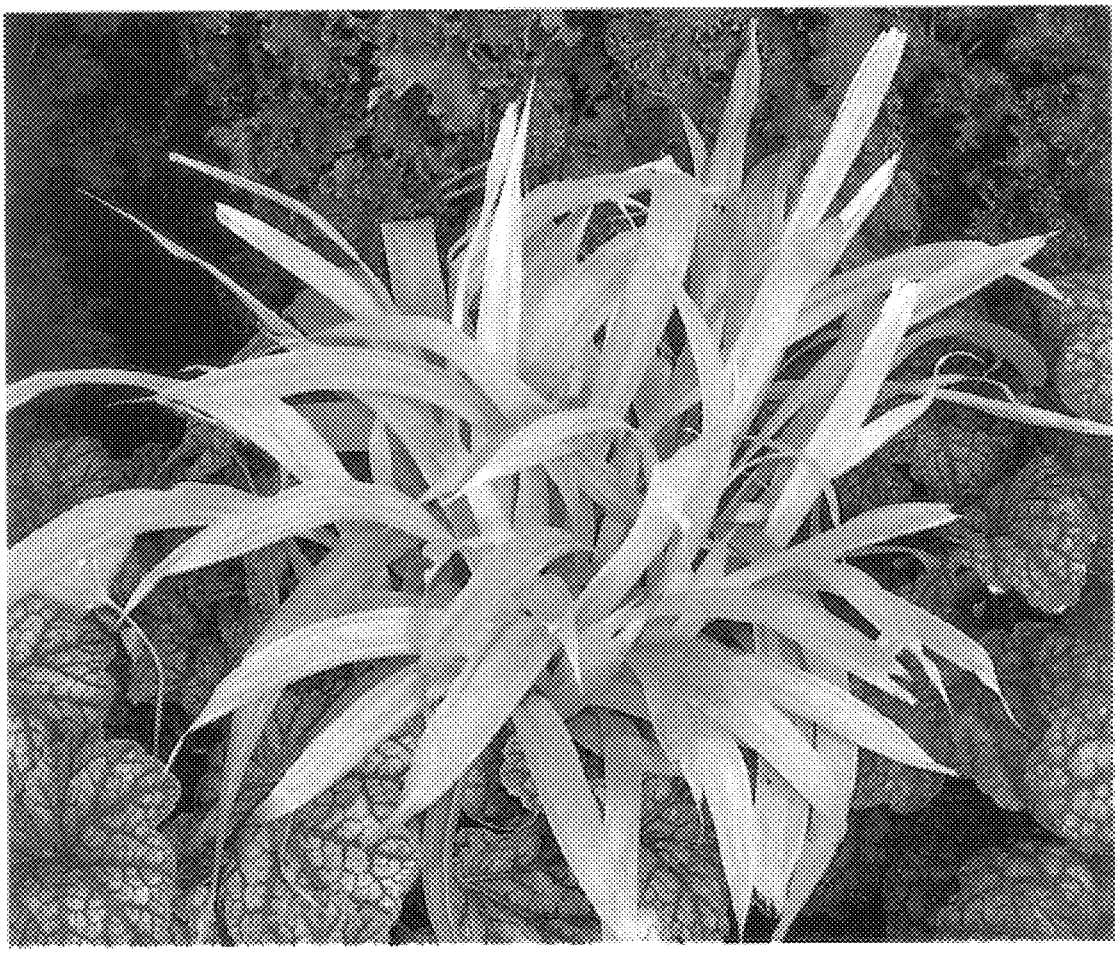

* * * * *